United States Patent [19]

Katz

[11] Patent Number: 4,798,536

[45] Date of Patent: Jan. 17, 1989

[54] HIGH STRENGTH FELDSPATHIC DENTAL PORCELAINS CONTAINING CRYSTALLINE LEUCITE

[75] Inventor: Sigmund Katz, West Orange, N.J.

[73] Assignee: American Thermocraft Corp., East Orange, N.J.

[21] Appl. No.: 124,459

[22] Filed: Dec. 1, 1987

Related U.S. Application Data

[63] Continuation-in-part of Ser. No. 50,011, May 15, 1987, abandoned, which is a continuation-in-part of Ser. No. 945,834, Dec. 23, 1986, abandoned.

[51] Int. Cl.⁴ .................. A61C 13/08; A61C 13/083; C03C 10/10
[52] U.S. Cl. .................. 433/212.1; 106/35; 433/199.1; 433/201.1; 433/202.1; 433/218; 433/222.1; 501/6; 501/32; 501/141; 501/143
[58] Field of Search ............... 106/35; 433/199, 201.1, 433/202.1, 206, 207, 212.1, 218, 222, 228.1; 501/6, 16, 21, 32, 141, 143

[56] References Cited

U.S. PATENT DOCUMENTS

| | | | |
|---|---|---|---|
| Re. 1,122 | 1/1861 | Moffitt | 433/199.1 |
| 2,000,285 | 5/1935 | Hoffman | 106/6 |
| 2,341,998 | 2/1944 | Lee et al. | 106/35 |
| 2,776,897 | 1/1957 | Hazelwood | 106/39 |
| 2,897,595 | 8/1959 | Lee | 32/8 |
| 2,920,971 | 1/1960 | Stookey | 106/39 |
| 3,052,982 | 10/1959 | Weinstein et al. | 32/8 |
| 3,052,983 | 9/1962 | Weinstein et al. | 32/12 |
| 3,069,773 | 12/1962 | Saffir | 32/8 |
| 3,181,240 | 5/1965 | Kerhart et al. | 32/8 |
| 3,423,830 | 1/1969 | Halpern et al. | 32/8 |
| 3,464,837 | 9/1969 | McLean et al. | 106/35 |
| 3,499,787 | 3/1970 | Inoue | 427/376.2 |
| 3,689,293 | 9/1972 | Beall | 106/39 |
| 3,732,087 | 5/1973 | Grossman | 65/33 |
| 3,922,155 | 11/1975 | Broemer et al. | 65/33 |
| 4,101,330 | 7/1978 | Burk et al. | 106/35 |
| 4,265,669 | 5/1981 | Starling et al. | 106/73.4 |
| 4,431,420 | 2/1984 | Adair | 433/199 |
| 4,431,451 | 2/1984 | Mable et al. | 106/35 |
| 4,433,958 | 2/1984 | Fellman et al. | 433/199 |
| 4,455,383 | 6/1984 | Panzera | 501/6 |
| 4,461,618 | 7/1984 | DeLuca et al. | 433/200 |
| 4,478,641 | 10/1984 | Adair et al. | 106/38.3 |
| 4,481,036 | 11/1984 | Panzera | 106/35 |
| 4,492,777 | 1/1985 | Denton et al. | 523/115 |
| 4,500,657 | 2/1985 | Kumar | 523/116 |
| 4,515,634 | 5/1985 | Wu et al. | 106/35 |
| 4,550,030 | 10/1985 | Ohi et al. | 433/212.1 |
| 4,551,099 | 11/1985 | Panzera | 433/212.1 |
| 4,557,691 | 12/1985 | Martin et al. | 433/199.1 |
| 4,585,417 | 4/1986 | Sozio et al. | 433/202.1 |
| 4,604,059 | 8/1986 | Klaus et al. | 433/217.1 |
| 4,604,366 | 8/1986 | Kacicz et al. | 106/35 |
| 4,645,454 | 2/1987 | Amdur et al. | 433/212.1 |

FOREIGN PATENT DOCUMENTS 189260  7/1986  European Pat. Off. ............ 501/143

OTHER PUBLICATIONS

Hahn, C., Teuchert, K. "Importance of the Glass Ceramic System $K_2O-Al_2O_3-SiO_2$ in Dental Porcelain", Ber. Dtsch. Keram. Ges. 1980 57 (9–10) pp. 208–214.

Primary Examiner—Prince E. Willis
Assistant Examiner—Linda D. Skaling
Attorney, Agent, or Firm—Kramer, Brufsky & Cifelli

[57] ABSTRACT

Translucent feldspathic dental porcelain compositions and dental restoration made therefrom exhibiting a crystalline leucite content of at least about 45% by weight, wherein said leucite crystallites exhibit a size of less than about 35 microns, comprising:

| Component | Percentage (by weight) |
|---|---|
| $SiO_2$ | 55–70 |
| $Al_2O_3$ | 16–20 |
| CaO | 0.5–5.0 |
| MgO | 0.5–5.0 |
| $Li_2O$ | 1.0–5.0 |
| $Na_2O$ | 2.0–5.0 |
| $K_2O$ | 12.5–22.5 |
| $Ce_2O_3$ | 0–1.0 | said dental restorations exhibit a compressive strength of at least about 125,000 p.s.i., a flexural strength of at least about 16,000 p.s.i., and a diametral tensile strength of at least about 6,000 p.s.i., thereby obviating the need for metal as ceramic supports.

13 Claims, No Drawings

HIGH STRENGTH FELDSPATHIC DENTAL PORCELAINS CONTAINING CRYSTALLINE LEUCITE

CROSS REFERENCE

This application is a continuation-in-part of copending application Ser. No. 050,011 filed on May 15, 1987, now abandoned, which application is a continuation-in-part of application Ser. No. 945,834 filed Dec. 23, 1986, now abandoned.

FIELD OF THE INVENTION

The present invention relates to a new family of dental porcelain compositions exhibiting greater flexural strength, compressive strength, diametral tensile strength and crystalline leucite content ($K_2O.Al_2O_3.4SiO_2$) than present commercial dental porcelains and are thus useful in the manufacture of porcelain dental restorations such as artificial teeth, crowns, bridges and the like which can be employed without metal supporting structures as heretofore required.

BACKGROUND OF THE INVENTION

Porcelain is one of the most important materials used in dentistry. It lends itself to the manufacture of the most esthetic dental restorations since it can be colored to closely resemble the teeth it must replace.

Porcelain exhibits excellent chemical qualities insofar as dental applications are concerned. It is insoluble in the normal fluids of the oral cavity and in practically any given food or drink likely to pass through the oral cavity. It is also chemically able to resist the acid or alkali materials frequently used for washing artifical teeth. Moreover, mammalian tissues are very tolerant of its presence and such tolerance remains even after years of continuous contact.

Porcelain does have, however, one great disadvantage. It is relatively fragile and repairs are difficult and costly. Because of the hazard of fragility, artificial dental crowns and bridges have heretofore been made using a metallic framework coated with a fused dental porcelain to provide the desired esthetics and strength.

The type of porcelain that is currently most often employed in dental restorations is typified by that described in the Weinstein et al patents, U.S. Pat. Nos. 3,052,982 and 3,052,983. The Weinstein et al patents address the problem of preparing a porcelain whose coefficient of thermal expansion will match that of the metal base so that excessive stress formation will not occur during the production of the restoration.

The solution proposed by Weinstein et al was to make a dental porcelain composed of two different frits, one having a high coefficient of expansion and the other having a much lower coefficient of expansion, to result in a porcelain having a coefficient of expansion intermediate between the two materials, and which will match the dental alloy employed as the base.

The major disadvantage of the metal supported porcelain restoration is the loss of translucency which is especially noticeable at the gingival margin area. The junction of the restoration with the tooth may lack the translucent esthetic quality desired even in the case of an all-porcelain margin. Also, the added complexity of waxing, casting and metal finishing requires an increased amount of labor for the production of the restoration. Still, it has been the most versatile restoration heretofore employed.

Mechanisms of strengthening ceramics, other than the use of metal ceramic systems, have primarily involved dispersion strengthening (aluminous core materials) and controlled crystallization (Dicor® castable glass ceramic from Dentsply International, Inc., York, Pa., and CeraPearl® castable glass ceramic from Kyocera, Inc., San Diego, Calif.). The aforementioned systems are not greatly different in their clinical strength. Color is applied to the surface of such cast glasses, which limits their potential for optimum esthetics.

An alternative to the cast-glass ceramic systems is the extrusion molded system which employs an epoxy die and a shrink-free (expansion/contraction controlled) system, for example, Cerestore® nonshrink alumina ceramic of Johnson & Johnson Dental Products, Inc. The extrusion molded and cast-glass ceramic systems exhibit disadvantages, including a high initial equipment cost and the fact that each system is somewhat labor intensive.

A further disadvantage of systems employing an aluminous core is the reduced translucency produced by the semi-opaque nature of the core materials. Both the cast ceramic systems and the dispersion strengthened systems also have an inherent disadvantage in the manner in which they might be joined to form multiple units. Satisfactory commercially feasible systems of joining alumina reinforced ceramic units have not been developed.

Accordingly, it is an object of the present invention to provide a high strength dental porcelain for use in making all-ceramic dentures, crowns and bridges, thereby obviating the need for a metal or ceramic support.

A further object of the present invention is to provide a dental porcelain composition which is translucent and exhibits the ability to accept colors producing a restoration exhibiting desirable dental shades.

A still further object of this invention is to provide artifical crowns and bridges with greater impact strength and hence greater resistance to chipping.

A still further object is to provide a high strength dental porcelain composition which can be used employing present laboratory equipment and eliminating the need for extensive heat treatment.

A still further object is to provide permanent dental restorations exhibiting high strength, i.e., a minimum compressive strength of at least about 125,000 p.s.i., a diametral tensile strength of at least about 6,000 p.s.i. and a flexural strength of at least about 16,000 p.s.i.

SUMMARY OF THE INVENTION

These as well as other objects and advantages can be achieved through the present invention which provides a translucent feldspathic dental porcelain composition useful for preparing dental restorations having a compressive strength of at least about 125,000 p.s.i., a diametral tensile strength of at least about 6,000 p.s.i., a flexural strength of at least about 16,000 p.s.i. and a crystalline leucite content of at least about 45% by weight, wherein said leucite crystallite exhibits a size of less than about 35 microns, preferably less than about 5 microns, comprising:

| Component | Percentage (by weight) |
|---|---|
| SiO$_2$ | 55–70 |
| Al$_2$O$_3$ | 16–20 |
| CaO | 0.5–5.0 |
| MgO | 0.5–5.0 |
| Li$_2$O | 1.0–5.0 |
| Na$_2$O | 2.0–5.0 |
| K$_2$O | 12.5–22.5 |
| Ce$_2$O$_3$ | 0–1.0 |

DETAILED DESCRIPTION OF THE INVENTION

The translucent feldspathic dental porcelain composition of the present invention can be made using a variety of feldspars, including Wyoming, Canadian, Norwegian, and Carolinian feldspars. These as well as other feldspars which have the following general composition are considered suitable for use in conjunction with the present invention:

| Component | Percentage (by weight) |
|---|---|
| SiO$_2$ | 64–67 |
| Al$_2$O$_3$ | 17–20 |
| CaO | 0.5–1.0 |
| K$_2$O | 12.0–14.0 |
| Na$_2$O | 1.0–3.0 |

Preferably, Wyoming feldspar is used in making the dental porcelain of the present invention. At least a portion of the K$_2$O, Al$_2$O$_3$ and SiO$_2$ in such feldspars is currently believed to be present in a crystalline leucite configuration. Although not wishing to be bound by any theory or mechanism, it is currently believed that such leucite crystallites serve as nuclei during the fusing and cooling process in order to initiate further crystalline leucite nucleation and growth in the magma. As the magma is cooled, the crystalline leucite becomes less soluble and precipitates out.

Na$_2$O is an inhibitor of leucite crystal growth during the fusing and cooling process. Low Na$_2$O in conjunction with high K$_2$O in the feldspar is believed to be responsible for the resulting high leucite content of the translucent feldspathic dental porcelain composition.

The feldspar is first culled to remove quartz, mica, and biotite. Next the feldspar is charged to a ball mill containing a grinding medium to reduce it to a fine powder, 95% of which passes through a 180 mesh screen. Then the feldspar is passed through a dry magnetic separator to remove any iron impurities that may be present. It is next further milled and screened through a 200 mesh screen.

The resultant powdered feldspar is blended with cerium oxide, if included, and a flux comprising any or all of the following: potassium nitrate, potassium silicate, lithium carbonate, calcium carbonate and magnesium oxide in quantities such that the resultant feldspathic dental porcelain, after fusing as herein-after described, comprises:

| Component | Percentage (by weight) |
|---|---|
| SiO$_2$ | 55–70 |
| Al$_2$O$_3$ | 16–20 |
| CaO | 0.5–5.0 |
| MgO | 0.5–5.0 |
| Li$_2$O | 1.0–5.0 |

-continued

| Component | Percentage (by weight) |
|---|---|
| Na$_2$O | 2.0–5.0 |
| K$_2$O | 12.5–22.5 |
| Ce$_2$O$_3$ | 0–1.0 |

Preferably, said resultant feldspathic dental porcelain composition comprises:

| Component | Percentage (by weight) |
|---|---|
| SiO$_2$ | 60–64 |
| Al$_2$O$_3$ | 16–19 |
| CaO | 0.5–2.0 |
| MgO | 0.5–1.5 |
| Li$_2$O | 1.0–3.0 |
| Na$_2$O | 2.0–4.0 |
| K$_2$O | 12.5–14.5 |
| Ce$_2$O$_3$ | 0–0.15 |

The quantity of flux needed will, of course, depend upon the particular composition of feldspar employed. Depending upon the initial fusing point of the feldspar, more or less flux will be needed in order that the fusing point is adjusted accordingly. For instance, a high fusing point feldspar will require more flux and a low fusing point feldspar, less flux.

The potassium oxide can be introduced by employing a combination of potassium nitrate and potassium silicate. It has surprisingly been found that this combination produces a much better product than either does alone.

From about 2 to about 7, preferably 3, wt % potassium nitrate can be used in the powdered dental porcelain composition of the present invention. The potassium nitrate functions to introduce potassium oxide into the silicate lattice, from which lattice the leucite crystals precipitate. The potassium oxide also lowers the fusing range.

From about 3 to about 10, preferably 5, wt % potassium silicate can be used in the powdered dental porcelain composition of the present invention. The potassium silicate functions in the same manner as the potassium nitrate, and the silicate tends to increase the silicate phase and to stabilize it such that leucite precipitation is more easily controlled resulting in the uniform distribution of leucite crystallites having a size of less than about 35 microns, preferably less than about 5 microns, throughout the glass matrix.

From about 2.5 to about 12.5, preferably from about 2.5 to about 7, and most preferably 3.5, wt % lithium carbonate can be used in the flux comprising the translucent feldspathic dental porcelain composition of the present invention. The lithium oxide is desired because it controls the fusing range without degrading other desirable properties. The incorporation of lithium oxide also functions to modify the viscosity during fusion so as to favor nucleation and crystalline leucite grain growth. The softer feldspars, for example, Carolinian feldspar, require less lithium carbonate than the harder feldspars, such as the Wyoming feldspar.

From about 0.75 to about 9, preferably from about 0.75 to about 5.5, and most preferably 2, wt% calcium carbonate can be used in the flux of the present invention. The calcium carbonate is desired because upon fusing it becomes calcium oxide which strengthens the glass phase and reduces its solubility in the presence of a high potassium oxide content.

From about 0.5 to about 5, preferably from about 0.5 to about 1.5, or most preferably 0.8, wt % magnesium oxide can be used in the translucent feldspathic dental porcelain composition of the present invention. The magnesium oxide is desired because it appears to function synergistically with the calcium oxide in strengthening the glass in relation to either alone.

From about 0 to about 1 wt %, preferably from about 0 to about 0.15 wt% cerium oxide can be used in the translucent feldspathic dental porcelain composition of the present invention. After fusion and cooling, without the incorporation of the cerium oxide, the resultant fused composition is extremely hard but can be milled by high impact comminution processes. Milling of such an extremely hard composition by attrition results in excessive fines and coarse particles, which are not useful since the resulting milled product cannot be wet. The cerium oxide in the composition of the present invention is desirable since it releases small amounts of oxygen at a point during the fusion where the viscosity is low enough such that bubbles are produced. The bubbles so created in the matrix allow for ready milling of the fused composition via both impact and attrition. The bubbles are also believed to provide extra surface for nucleation.

Nucleating agents, such as niobium oxide, can also be included in the translucent feldspathic dental porcelain composition in order to enhance leucite crystal formation. The addition of nucleating agents for such purposes is well known to those skilled in the art.

The unfired feldspathic mineral is opaque. Dental porcelain, of course, is highly translucent and is largely vitreous. By addition of potassium oxide and firing, most of the feldspathic mineral is converted to a vitreous phase.

The translucent feldspathic mixture, after blending, is charged into saggers and fused to form a vitreous body containing a uniform dispersion of leucite nuclei therein. The fusion can be carried out at about 2150° to about 2350° F., preferably about 2250° F., for from about 2 to about 10, preferably about 5, hours. After the fusion, the porcelain composition is furnace-cooled at about 5° F./min to about 1900° F., held there for from about one to about four hours, and then quenched by immersion into water. The above fusion provides the requisite translucency, requisite crystalline leucite content, and desired leucite crystallite size of less than about 35 microns, preferably less than about 5 microns. The slow cooling to about 1900° F. is essential for crystalline leucite nucleation and growth. Quenching at about 1900° F. is also essential in order to arrest further growth of crystalline leucite such that the requisite translucency is provided. The quenched fused porcelain chunks are dried and then crushed and reduced to a fine powder by, for example, ball milling. Preferably the powder is fine enough to pass through a 180 to 200 mesh screen.

Since the feldspathic dental porcelain composition of the present invention is translucent, it is able to accept pigments and produce a restoration after firing exhibiting desirable dental shades. The usual pigments, such as chromates, vanadates, and manganates can be added to the feldspathic dental porcelain composition in small amounts, such as 0.5–1.5 weight percent, as well as opacifiers such as tin oxide, if desired. The thermal expansion of the porcelain is controlled to match that of the refractory die described below.

After the porcelain powder has been prepared and blended with the pigments, it is then employed in making dental restorations in the conventional manner; however, use of a metal or ceramic support is not required.

The general technique for the construction of a porcelain dental restoration (i.e. crown or bridge), is the following: first an impression is taken of the area that has been prepared to receive the dental restoration. A refractory die is prepared from the impression. The porcelain powder is then mixed with water to form a slurry, which is then applied to the refractory die by standard procedures.

Once the dental porcelain material is in its predetermined and desired shape, it is fired as is conventional for preparation of the various dental porcelain constructions in the art. The composition in its predetermined shape is first dried and then fired at a temperature and for a time such that the dental porcelain material fuses together as is conventional in the art for the preparation of a fired dental porcelain.

Typically, the composition of the present invention is fired at a temperature of from about 1875° F. to about 1975° F., preferably 1900° F., for about 30 seconds. The furnace temperature is raised from about 1000° F. at the time of insertion to the desired temperature at a rate of from about 75° F. to about 125° F./minute, preferably 100° F./minute.

Once the composition has been fired, a dental restoration in the predetermined shape is provided, i.e., in the shape of a crown or bridge, for example, as discussed above.

By employing the composition of the present invention, the fused translucent feldspathic dental porcelain restoration thus obtained exhibits a compressive strength of at least about 125,000 p.s.i., typically about 140,000 p.s.i.; a diametral tensile strength of at least about 6,000 p.s.i., typically about 10,000 p.s.i.; a flexural strength of at least about 16,000 p.s.i., typically about 20,000 p.s.i.; and a crystalline leucite content of at least about 45% by weight, typically about 55 to about 75% by weight; said leucite crystallites exhibiting a size of less than about 35 microns, preferably less than about 5 microns. These physical characteristics provide a dental composition with sufficient strength to obviate the need for a metal or ceramic support. Accordingly, the practitioner can make the desired dental porcelain structure in one step.

The coefficient of thermal expansion of the high strength porcelain compositions of the present invention are significantly higher than the conventional porcelain compositions currently used for porcelain-fused-to-metal applications. As a result, the high strength porcelains of the present invention cannot be fused to the porcelain-fused-to-metal alloys currently available.

While the porcelain compositions of the present invention cannot be fused to any currently available porcelain-fused-to-metal alloys, they can be bonded to conventional dental metal substrates, if desired, using conventional resin (filled or unfilled) bonding techniques.

The following examples are intended to illustrate, but not to limit, the present invention. Unless otherwise stated, all percentages and parts are by weight.

EXAMPLE 1

Wyoming Feldspar, having the following composition:

65.3 wt % SiO$_2$
19.1 wt % Al$_2$O$_3$
0.1 wt % CaO
3.2 wt % Na$_2$O
12.1 wt % K$_2$O
0.2 wt % *L.O.I.

*L.O.I.=Loss on ignition.

is culled to remove quartz, mica, and biotite. Next, the feldspar is charged into a ball mill containing a grinding medium and reduced to about 180 mesh. Then, the feldspar is passed through a dry magnetic separator to remove any iron impurities. It may then be further milled for approximately 2 to 4 hours and screened through a 200 mesh screen.

The translucent feldspathic dental porcelain composition of the present invention was prepared by blending the components listed in Table I:

TABLE I

| Component | Grams |
|---|---|
| Wyoming Feldspar | 85.74 |
| KNO$_3$ | 3.00 |
| K$_2$O SiO$_2$(1:2.5) | 5.00 |
| Li$_2$CO$_3$ | 3.50 |
| CaCO$_3$ | 1.90 |
| MgO | 0.76 |
| Ce$_2$O$_3$ | 0.10 |
| | 100.00 |

After weighing the raw materials, the components were blended, ball milled for 1 hour, transferred to a high alumina body sagger which was coated with a parting agent, for example, Al$_2$O$_3$, and heated to 2250° F. (at a heat-up rate of 400° F./hour) and maintained at that temperature for five hours. After fusion, the porcelain magma was cooled at about 5°/min to 1900° F. and held at 1900° F. for from about 1 to about 4 hours. The magma was then quenched in water and dried. The porcelain composition so produced was crushed and ball milled such that the resulting particles pass through a 200 mesh screen.

The addition of pigments was accomplished by preparing a master batch at a pigment concentration of about 10% by weight. The master batch was prepared by the addition of the required pigment to a 1 kilogram batch of the translucent feldspathic dental porcelain composition and ball milling the mixture in order to disperse the pigments uniformly throughout.

To a 15 kilogram batch of the translucent feldspathic dental porcelain composition was added the following pigment master batch to produce a composition which, upon firing, resulted in a restoration with a desirable dental shade:

| Amount (grams) | Pigment (10% concentration) |
|---|---|
| 2.25 | Iron/Chrome/Zinc |
| 35.0 | Zirconium Praseodymium |
| 25.0 | Zirconium Vanadium Indium |
| 9.0 | Coral Brown |

The mixture was then ball milled to evenly disperse the pigments throughout.

EXAMPLE 2

The translucent feldspathic dental porcelain composition obtained from Example 1 and control 1 (Pencraft Porcelain from American Thermocraft Corp., 60 Franklin Street, West Orange, N.J. 07017) were formed into appropriate shapes for physical testing.

These structures were then dried at 1000° F. for 6-8 minutes, followed by firing in an electric furnace to 1900° F. (at a heat-up rate of 100° F./min) and maintained at that temperature for 30 seconds and then allowed to cool to room temperature in air.

The following physical properties were measured for the translucent feldspathic dental porcelains so produced:

TABLE II

| | Example 2 | Control 1** |
|---|---|---|
| Compressive Strength (p.s.i.) | 140,000 | 50,000 |
| Diametral Tensile Strength (p.s.i.) | 12,000 | 6,000 |
| Flexural Strength (p.s.i.) | 20,000 | 11,000 |
| *Leucite Content (% by weight) | Example 2 was about 40% greater than control 1. | |
| Coefficient of Thermal Expansion (in./in. °C.) | 18 × 10$^{-6}$ | 13.2 × 10$^{-6}$ |

*Estimated by Xray Diffraction.
**Fired to its fully matured temperature of 1800° F.

EXAMPLE 3

Preparation of a Dental Restoration of the Present Invention

An impression was taken of the area that had been prepared to receive the dental restoration. A refractory die was prepared from the impression. The die was soaked in water so as not to absorb the water from the porcelain slurry when applied thereto. The feldspathic translucent dental porcelain composition of Example 1 was mixed with water to form a slurry. The slurry was applied to the die using a spatula and forming a rough facsimile of the desired dental restoration. Gingival porcelain was built first. Then incisal porcelain was blended over the gingival porcelain. The water was then removed by a combination of vibration and absorption with a tissue. The exact configuration of the desired restoration was then carved by a dental laboratory technician.

The unfired restoration was dried outside a furnace held at 1000° F. for 6-8 minutes. It was then placed in the furnace and the temperature raised to 1900° F. and held for 30 seconds (at a heat-up rate of 100° F./min). The restoration was then removed from the furnace and allowed to cool to room temperature in air. Appropriate porcelain additions were made in order to perfect the configuration of the restoration, and the restoration was refired as necessary. Between firings, adjustments were made with appropriate grinding instruments. In this manner, an all-porcelain dental restoration was obtained exhibiting sufficiently high strength such that a conventional metal or ceramic support was not necessary for the resulting restoration to meet all current dental requirements.

While the invention has been described in accordance with desirable embodiments and details of procedure, it is obvious that many changes and modifications may be made in the details thereof and in the characteristics of the compositions and articles obtained therefrom without departing from the spirit of the invention.

What is claimed is:

1. A method of preparing a translucent feldspathic dental composition exhibiting a crystalline leucite content of at least about 45% by weight, wherein said leucite crystallites exhibit a size of less than about 35 microns, comprising the steps of:

(a) culling a feldspar having the composition comprising:

| Component | Percentage (by weight) |
|---|---|
| $SiO_2$ | 64–67 |
| $Al_2O_3$ | 17–20 |
| CaO | 0.5–1.0 |
| $K_2O$ | 12.0–14.0 |
| $Na_2O$ | 1.0–3.0 | to remove quartz, mica and biotite;
(b) grinding said feldspar;
(c) passing said ground feldspar through a 200 mesh screen;
(d) blending the screened feldspar with potassium nitrate, potassium silicate, lithium carbonate, calcium carbonate, magnesium oxide, cerium oxide, alumina and/or aluminum silicate in quantities such that the resultant feldspathic dental porcelain composition, after fusion, comprises:

| Component | Percentage (by weight) |
|---|---|
| $SiO_2$ | 55–70 |
| $Al_2O_3$ | 16–20 |
| CaO | 0.5–5.0 |
| MgO | 0.5–5.0 |
| $Li_2O$ | 1.0–5.0 |
| $Na_2O$ | 2.0–5.0 |
| $K_2O$ | 12.5–22.5 |
| $Ce_2O_3$ | 0–1.0 |

(e) fusing said feldspathic dental porcelain composition at from about 2150° to about 2350° for from about 2 to about 10 hours at a heat-up rate of about 400° F./hour, thereby forming a magma;
(f) cooling said magma at about 5° F./minute to about 1900° F.;
(g) holding said cooled magma at about 1900° F. for from about one to about four hours;
(h) quenching said cooled magma in water; and
(i) milling said quenched magma such that 95% thereof passes through a 180 mesh screen, thereby forming said translucent feldspathic dental porcelain composition.

2. A method according to claim 1 wherein at least a portion of the $K_2O$, $Al_2O_3$ and $SiO_2$ in said feldspar is present in a crystalline leucite configuration.

3. A method according to claim 2 wherein said feldspar is Wyoming feldspar.

4. A method according to claim 1 further comprising the step of passing said ground feldspar through a dry magnetic separator to remove iron after grinding.

5. A method according to claim 1 wherein the fusing temperature is about 2250° F.

6. A method according to claim 5 wherein the fusing temperature is maintained for about 5 hours.

7. A translucent feldspathic dental porcelain restoration exhibiting a minimum crystalline leucite content of about 45% by weight, wherein said leucite crystallites exhibit a size of less than about 35 microns; a compressive strength of at least about 125,000 p.s.i.; a diametral tensile strength of at least about 6,000 p.s.i.; and a flexural strength of at least about 16,000 p.s.i.; said restoration consisting essentially of a translucent feldspathic dental porcelain comprising:

| Component | Percentage (by weight) |
|---|---|
| $SiO_2$ | 55–70 |
| $Al_2O_3$ | 16–20 |
| CaO | 0.5–5.0 |
| MgO | 0.5–5.0 |
| $Li_2O$ | 1.0–5.0 |
| $Na_2O$ | 2.0–5.0 |
| $K_2O$ | 12.5–22.5 |
| $Ce_2O_3$ | 0–1.0 |

8. A translucent feldspathic dental porcelain restoration according to claim 7 wherein the leucite crystallites exhibit a size of less than about 5 microns.

9. A translucent feldspathic dental porcelain restoration according to claim 7 wherein said translucent feldspathic dental porcelain comprises:

| Component | Percentage (by weight) |
|---|---|
| $SiO_2$ | 60–64 |
| $Al_2O_3$ | 16–19 |
| CaO | 0.5–2.0 |
| MgO | 0.5–1.5 |
| $Li_2O$ | 1.0–3.0 |
| $Na_2O$ | 2.0–4.0 |
| $K_2O$ | 12.5–14.5 |
| $Ce_2O_3$ | 0–0.15 |

10. A translucent feldspathic dental porcelain restoration according to claim 7 wherein said translucent feldspathic dental porcelain further comprises at least one pigment.

11. A translucent feldspathic dental porcelain restoration according to claim 9 wherein said translucent feldspathic dental porcelain further comprises at least one pigment.

12. A translucent feldspathic dental porcelain restoration according to claim 10 wherein said pigment is selected from the group consisting of chromates, vanadates, manganates, and mixtures thereof.

13. A translucent feldspathic dental porcelain restoration according to claim 7 exhibiting a coefficient of thermal expansion of $18 \times 10^{-6}$ in./in. °C.

* * * * *